Figure 1:
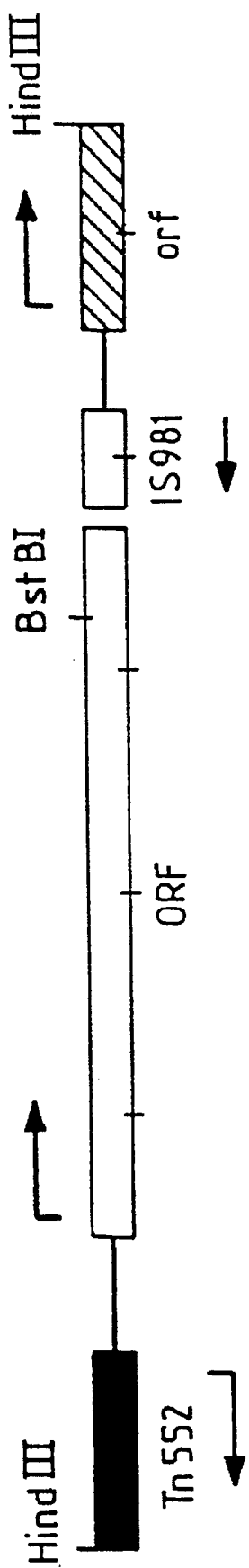

United States Patent [19]
Prevots et al.

[11] Patent Number: 5,658,770
[45] Date of Patent: Aug. 19, 1997

[54] NUCLEIC ACID SEQUENCE AND PLASMIDS COMPRISING AT LEAST ONE PHAGE RESISTANCE MECHANISM, BACTERIA IN WHICH THEY ARE PRESENT, AND THEIR USE

[75] Inventors: Fabien Prevots; Elisabeth Remy, both of Toulouse; Paul Ritzenthaler, Castanet, all of France

[73] Assignees: Sanofi, Paris; Elf Aquitaine, Courbevoie, both of France

[21] Appl. No.: 286,325

[22] Filed: Aug. 4, 1994

[30] Foreign Application Priority Data

Aug. 9, 1993 [FR] France ................... 93 09777

[51] Int. Cl.$^6$ ............. C07H 21/04; C12P 21/00; C12N 15/00
[52] U.S. Cl. ............ 435/172.2; 435/69.1; 435/172.3; 435/320.1; 536/23.7
[58] Field of Search ............... 435/172.3, 69.1, 435/172.1; 536/23.7

[56] References Cited

U.S. PATENT DOCUMENTS 4,883,756  11/1989  Klaenhammer et al. ............ 435/252.3

FOREIGN PATENT DOCUMENTS

| A-0 208 468 | 1/1987 | European Pat. Off. . |
| 0208468A2 | 1/1987 | European Pat. Off. . |
| A-0 246 909 | 11/1987 | European Pat. Off. . |
| 0355036 | 2/1990 | European Pat. Off. . |
| 0452224A1 | 10/1991 | European Pat. Off. . |
| WOA9205260 | 4/1992 | WIPO . |

OTHER PUBLICATIONS

Van Belkum et al., *Applied & Environmental Microbiology*, 55(5): 1187–1191 (May 1989).
Sing et al., *Applied & Environmental Microbiology*, 51(6): 1264–1271 (Jun. 1986).
Sanders et al., *Applied and Environmental Microbiology*, vol. 46, No. 5, 1983, 1125–1133.
Steenson et al., *Applied and Environmental Microbiology*, vol. 50, No. 4, Oct. 1985, 851–858.
Jarvis et al., *Applied and Environmental Microbiology*, vol. 55, No. 6, Jun. 1989, 1537–1543.
Hill et al., *Applied and Environmental Microbiology*, vol. 55, No. 7, Jul. 1989, 1684–1689.
Hill et al., *Applied and Environmental Microbiology*, vol. 56, No. 7, Jul. 1990, 2255–2258.
Prevots et al., *Applied and Environmental Microbiology*, vol. 56, No. 7, Jul. 1990, 2180–2185.
Klaenhammer, *Journal of Dairy Science*, vol. 72, No. 12, 1989, 3429–3443.
Vlegels et al., *Netherlands Milk and Dairy Journal*, vol. 43, 1989, 245–259.
Jarvis, *Applied and Environmental Microbiology*, Mar. 1988, 777–783.
Lerayer et al., *Revista De Microbiologia*, vol. 20, No. 2, Apr.–Jun. 1989, 197–209.
Sanders et al., *Applied and Environmental Microbiology*, vol. 47, No. 5, May 1984, 979–985.
van Belkum et al., *Applied and Environmental Microbiology*, vol. 55, No. 5, May 1989, 1187–1191.
Sanders, *Biochemie*, vol. 70, 1988, 411–421.
Coffey et al., *Netherlands Milk and Dairy Journal*, vol. 43, 1989, 229–244.
Froseth et al., *Journal of Dairy Science*, vol. 71, 1988, 275–284.
Laible et al., *Journal of Dairy Science*, vol. 70, 1987, 2211–2219.
Steele et al., *Plasmid*, vol. 22, No. 1, 1989, 32–43.
Josephson et al., *Plasmid*, vol. 23, No. 1, Jan. 1990, 71–75.
Klaenhammer et al., *Journal of General Microbiology*, vol. 131, Jun. 1985, 1531–1541.
Gautier et al., *Applied and Environmental Microbiology*, vol. 53, No. 5, May 1987, 923–927.

*Primary Examiner*—James Ketter
*Assistant Examiner*—John S. Brusca
*Attorney, Agent, or Firm*—Foley & Lardner

[57] ABSTRACT

The invention relates to a DNA sequence of about 1.9 kb comprising at least one phage resistance mechanism, said sequence being obtained from the HindIII—HindIII DNA sequence of 3.3 kb contained in the strain *Lactococcus lactis* ssp *lactis*, deposited in the CNCM under no. I-945, by the PCR method.

5 Claims, 2 Drawing Sheets

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
      ( A ) LENGTH: 1875 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
      ( A ) ORGANISM: Lactococcus lactis ( i x ) FEATURE:
      ( A ) NAME/KEY: CDS
      ( B ) LOCATION: 202..1821

( x i ) SEQUENCE DESCRIPTION: SEQ ID NO: 1:

```
GAACATAGAA  TAGATTACGG  GTTAATGGAC  AATAAATGCA  AACGATTTTG  AGAAATTTAA   60

TAAGAAAAGA  AGAGTGTCCA  GAAAATGACC  ATTTTCTGAA  CGCCATATTA  AAAATTTTTT  120

GATAATTCCC  AATATATTAT  AATATAGCTT  CAATGTTAAA  ATTTATATGA  TATAATATAA  180

GAAAATTTTT  AAAAAAATAG A  ATG GAT ATA ATA ATG GAC TTT AAA ACT ATG        231
                          Met Asp Ile Ile Met Asp Phe Lys Thr Met
                           1               5                  10

TTA AGC TAT CTT GTA AGT CAA GAT GAT GAA ATT TCT TTA AGA AAT GAT         279
Leu Ser Tyr Leu Val Ser Gln Asp Asp Glu Ile Ser Leu Arg Asn Asp
             15                  20                  25

ATT AAA CAT GAA GAA GTA TAT AAA ATT TTA GAG AAT AAG TTT GCT TCT         327
Ile Lys His Glu Glu Val Tyr Lys Ile Leu Glu Asn Lys Phe Ala Ser
         30                  35                  40

ATA ATG CCG AAG TTT AAA ACA AAA GGT TAT AAG TTT AAA GAT ACT ACT         375
Ile Met Pro Lys Phe Lys Thr Lys Gly Tyr Lys Phe Lys Asp Thr Thr
         45                  50                  55

GAA GTT TTG ACA TTC GCT AAA TTT GTA TTT TTG CTA CAA GAG TGG GGG         423
Glu Val Leu Thr Phe Ala Lys Phe Val Phe Leu Leu Gln Glu Trp Gly
     60                  65                  70

TTG AAG GAT ATA CAG TTT TAT AAG AAC ACT AAT AGT TTC TTA TTT GGA         471
Leu Lys Asp Ile Gln Phe Tyr Lys Asn Thr Asn Ser Phe Leu Phe Gly
 75                  80                  85                  90

TAT ATT ATA CCG CAA ATT AAT AAA GAA TTT GAT TTA TTG AGA TTT GGG         519
```

-continued

```
              Tyr  Ile  Ile  Pro  Gln  Ile  Asn  Lys  Glu  Phe  Asp  Leu  Leu  Arg  Phe  Gly
                             95                       100                      105

GAA  AAT  TAC  AAT  ATT  AGT  ATA  GAA  CTC  AAA  AGT  AAA  ACA  ACA  GTA  GAA                567
Glu  Asn  Tyr  Asn  Ile  Ser  Ile  Glu  Leu  Lys  Ser  Lys  Thr  Thr  Val  Glu
               110                      115                      120

GCA  CAA  AAG  CAA  CAA  CTT  TGT  AAG  AAC  TAT  TTT  TAC  CTA  AAT  TTT  TTA                615
Ala  Gln  Lys  Gln  Gln  Leu  Cys  Lys  Asn  Tyr  Phe  Tyr  Leu  Asn  Phe  Leu
               125                      130                      135

TCA  ACT  AAA  ACT  AGG  TAT  ATT  AGT  ATA  TCC  CCA  GAT  ATA  TCT  AGT  TAC                663
Ser  Thr  Lys  Thr  Arg  Tyr  Ile  Ser  Ile  Ser  Pro  Asp  Ile  Ser  Ser  Tyr
          140                      145                      150

ATA  GAA  TAT  ATT  CCA  AGT  GAA  AAT  AAG  TAT  ATC  AAT  TTA  AGT  GGA  ACT                711
Ile  Glu  Tyr  Ile  Pro  Ser  Glu  Asn  Lys  Tyr  Ile  Asn  Leu  Ser  Gly  Thr
155                      160                      165                      170

GAA  ATT  TGT  GAT  ATT  ATT  ATT  AAA  CAA  GAG  TTT  TTA  GAG  TAT  AAT  ACA                759
Glu  Ile  Cys  Asp  Ile  Ile  Ile  Lys  Gln  Glu  Phe  Leu  Glu  Tyr  Asn  Thr
                    175                      180                      185

AAA  GAG  GTT  GAT  AGT  TTT  TTT  GAT  ATA  AAA  AAT  TAT  TTA  GTT  TCT  CCT                807
Lys  Glu  Val  Asp  Ser  Phe  Phe  Asp  Ile  Lys  Asn  Tyr  Leu  Val  Ser  Pro
               190                      195                      200

TTC  AAT  GAT  GTT  GAA  AAA  TTT  CTT  GAT  GAT  AAA  TAT  TTT  TTA  ACA  CCT                855
Phe  Asn  Asp  Val  Glu  Lys  Phe  Leu  Asp  Asp  Lys  Tyr  Phe  Leu  Thr  Pro
          205                      210                      215

CAC  CAA  GAC  CAG  ATT  GTT  AAA  GAA  ATT  ACT  GAA  CCA  AGT  GAC  AAA  AAA                903
His  Gln  Asp  Gln  Ile  Val  Lys  Glu  Ile  Thr  Glu  Pro  Ser  Asp  Lys  Lys
220                      225                      230

ACT  TTT  GGT  ATA  AAA  GGA  AAT  CCA  GGA  ACA  GGA  AAA  TCT  TTG  CTA  GTT                951
Thr  Phe  Gly  Ile  Lys  Gly  Asn  Pro  Gly  Thr  Gly  Lys  Ser  Leu  Leu  Val
235                      240                      245                      250

TAC  CAT  ATA  TGT  AAA  AAA  TTA  ATG  GAG  AAA  AAT  AAA  AGA  GTT  GCT  ATA                999
Tyr  His  Ile  Cys  Lys  Lys  Leu  Met  Glu  Lys  Asn  Lys  Arg  Val  Ala  Ile
                    255                      260                      265

GTT  CAT  GGA  GCA  AAT  CTA  AAT  AAT  GGT  CAA  CAA  AGA  TTA  GCT  CTG  CGT                1047
Val  His  Gly  Ala  Asn  Leu  Asn  Asn  Gly  Gln  Gln  Arg  Leu  Ala  Leu  Arg
               270                      275                      280

GGT  TTC  ACA  ATT  TTT  CCT  GTT  AAA  TCG  ATC  ATA  GAG  GTA  TTA  GAT  AAT                1095
Gly  Phe  Thr  Ile  Phe  Pro  Val  Lys  Ser  Ile  Ile  Glu  Val  Leu  Asp  Asn
          285                      290                      295

GCA  GAC  AAA  TAC  GAT  TAC  ATT  GTT  GTT  GAC  GAA  GCT  CAA  CGT  CTA  AGA                1143
Ala  Asp  Lys  Tyr  Asp  Tyr  Ile  Val  Val  Asp  Glu  Ala  Gln  Arg  Leu  Arg
     300                      305                      310

CAA  GAC  TTA  GGA  GAA  CAA  TAT  ACT  AAA  TTG  GTT  GAT  ACT  ATT  GAA  AAT                1191
Gln  Asp  Leu  Gly  Glu  Gln  Tyr  Thr  Lys  Leu  Val  Asp  Thr  Ile  Glu  Asn
315                      320                      325                      330

TCT  CAA  ACA  AAA  TTT  ATT  ATC  TCA  CTA  GAT  GGA  AGA  CAA  ACT  TTG  AAT                1239
Ser  Gln  Thr  Lys  Phe  Ile  Ile  Ser  Leu  Asp  Gly  Arg  Gln  Thr  Leu  Asn
               335                      340                      345

AAA  TAT  GAA  ATA  GAA  GAA  AAT  TCC  ATA  AAA  TTA  TTT  AAA  TAT  ATA  AAA                1287
Lys  Tyr  Glu  Ile  Glu  Glu  Asn  Ser  Ile  Lys  Leu  Phe  Lys  Tyr  Ile  Lys
          350                      355                      360

AAT  AAA  GGA  GTA  ACT  TTT  AGT  CTT  AAA  GAT  AAG  TTT  AGA  ACT  AAC  CCA                1335
Asn  Lys  Gly  Val  Thr  Phe  Ser  Leu  Lys  Asp  Lys  Phe  Arg  Thr  Asn  Pro
               365                      370                      375

GAA  ATG  AGC  AAA  TTT  ATC  CAA  CTT  CTA  TTC  AAA  ATA  CCC  ATG  TAT  AAA                1383
Glu  Met  Ser  Lys  Phe  Ile  Gln  Leu  Leu  Phe  Lys  Ile  Pro  Met  Tyr  Lys
          380                      385                      390

AAA  ATA  GAT  TTA  ATT  TCA  AAC  ATA  GAT  CAT  AAT  ATT  ATA  ATT  AAA  TAT                1431
Lys  Ile  Asp  Leu  Ile  Ser  Asn  Ile  Asp  His  Asn  Ile  Ile  Ile  Lys  Tyr
395                      400                      405                      410

TTT  GAT  AAC  AGA  GAA  TCG  GGA  AAT  GAA  TAT  ATT  TCC  GAT  ATG  GAT  TCA                1479
```

```
        Phe  Asp  Asn  Arg  Glu  Ser  Gly  Asn  Glu  Tyr  Ile  Ser  Asp  Met  Asp  Ser
                       415                 420                           425

AAC  TCA  GAT  TGG  GAA  GTA  CTT  AAT  TAC  ACG  AAG  GAT  AGA  TTT  AGG  AAA     1527
        Asn  Ser  Asp  Trp  Glu  Val  Leu  Asn  Tyr  Thr  Lys  Asp  Arg  Phe  Arg  Lys
                       430                 435                           440

ACA  GGA  ATT  GGT  AAA  ATG  TGT  GGT  AAT  GGT  TTA  ACA  TCA  CAT  AGT  ATT     1575
        Thr  Gly  Ile  Gly  Lys  Met  Cys  Gly  Asn  Gly  Leu  Thr  Ser  His  Ser  Ile
                       445                 450                           455

ATC  GGT  CAA  GAA  TTT  GAT  AAA  GTT  ATT  ATA  CCT  TTG  GAT  TCG  AAT  TTT     1623
        Ile  Gly  Gln  Glu  Phe  Asp  Lys  Val  Ile  Ile  Pro  Leu  Asp  Ser  Asn  Phe
                       460                 465                           470

TTT  TAT  AAA  GAA  CAA  AAA  ATA  ATT  GAT  AGT  AAA  ACG  GGT  GAA  AGT  AAA     1671
        Phe  Tyr  Lys  Glu  Gln  Lys  Ile  Ile  Asp  Ser  Lys  Thr  Gly  Glu  Ser  Lys
        475                 480                           485                      490

GTT  TTT  AAA  TTA  TTG  GAA  ACG  ACT  GAT  AAT  TTT  TAC  CCA  CTT  GAA  AAA     1719
        Val  Phe  Lys  Leu  Leu  Glu  Thr  Thr  Asp  Asn  Phe  Tyr  Pro  Leu  Glu  Lys
                            495                 500                           505

ATG  TTA  TAT  CAA  AAT  CTT  ACT  CGC  ACA  AGG  GGA  AAA  ATA  GAA  TTT  GTA     1767
        Met  Leu  Tyr  Gln  Asn  Leu  Thr  Arg  Thr  Arg  Gly  Lys  Ile  Glu  Phe  Val
                       510                 515                           520

ATT  ATT  GGA  AAT  CGT  TCA  ATT  TTT  AAT  GAA  ATA  TGT  GGA  TTG  CTA  GAT     1815
        Ile  Ile  Gly  Asn  Arg  Ser  Ile  Phe  Asn  Glu  Ile  Cys  Gly  Leu  Leu  Asp
                       525                 530                           535

AGT  TTA  TAAAGTTCTG  TCTCAAAGTT  AAAAAAAGTG  AAATCACTCG  CAACAGAACA              1871
        Ser  Leu
             540

GTTT                                                                              1875

( 2 ) INFORMATION FOR SEQ ID NO: 2:

( i ) SEQUENCE CHARACTERISTICS:
                        ( A ) LENGTH: 540 amino acids
                        ( B ) TYPE: amino acid
                        ( D ) TOPOLOGY: linear ( i i ) MOLECULE TYPE: protein ( x i ) SEQUENCE DESCRIPTION: SEQ ID NO: 2:

Met  Asp  Ile  Ile  Met  Asp  Phe  Lys  Thr  Met  Leu  Ser  Tyr  Leu  Val  Ser
        1                 5                      10                      15

Gln  Asp  Asp  Glu  Ile  Ser  Leu  Arg  Asn  Asp  Ile  Lys  His  Glu  Glu  Val
                       20                 25                      30

Tyr  Lys  Ile  Leu  Glu  Asn  Lys  Phe  Ala  Ser  Ile  Met  Pro  Lys  Phe  Lys
                  35                      40                 45

Thr  Lys  Gly  Tyr  Lys  Phe  Lys  Asp  Thr  Thr  Glu  Val  Leu  Thr  Phe  Ala
             50                      55                 60

Lys  Phe  Val  Phe  Leu  Leu  Gln  Glu  Trp  Gly  Leu  Lys  Asp  Ile  Gln  Phe
        65                      70                 75                           80

Tyr  Lys  Asn  Thr  Asn  Ser  Phe  Leu  Phe  Gly  Tyr  Ile  Ile  Pro  Gln  Ile
                            85                 90                           95

Asn  Lys  Glu  Phe  Asp  Leu  Leu  Arg  Phe  Gly  Glu  Asn  Tyr  Asn  Ile  Ser
                       100                 105                      110

Ile  Glu  Leu  Lys  Ser  Lys  Thr  Thr  Val  Glu  Ala  Gln  Lys  Gln  Gln  Leu
                  115                     120                 125

Cys  Lys  Asn  Tyr  Phe  Tyr  Leu  Asn  Phe  Leu  Ser  Thr  Lys  Thr  Arg  Tyr
             130                     135                 140

Ile  Ser  Ile  Ser  Pro  Asp  Ile  Ser  Tyr  Ile  Glu  Tyr  Ile  Pro  Ser
        145                     150                 155                      160

Glu  Asn  Lys  Tyr  Ile  Asn  Leu  Ser  Gly  Thr  Glu  Ile  Cys  Asp  Ile  Ile
```

|     |     |     |     |     |     |     | 165 |     |     |     |     | 170 |     |     |     |     | 175 |     |     |
|-----|-----|-----|-----|-----|-----|-----|-----|-----|-----|-----|-----|-----|-----|-----|-----|-----|-----|-----|-----|

Ile Lys Gln Glu Phe Leu Glu Tyr Asn Thr Lys Glu Val Asp Ser Phe
              180                   185                 190

Phe Asp Ile Lys Asn Tyr Leu Val Ser Pro Phe Asn Asp Val Glu Lys
          195                 200             205

Phe Leu Asp Asp Lys Tyr Phe Leu Thr Pro His Gln Asp Gln Ile Val
    210                 215             220

Lys Glu Ile Thr Glu Pro Ser Asp Lys Lys Thr Phe Gly Ile Lys Gly
225             230                 235                     240

Asn Pro Gly Thr Gly Lys Ser Leu Leu Val Tyr His Ile Cys Lys Lys
              245             250                 255

Leu Met Glu Lys Asn Lys Arg Val Ala Ile Val His Gly Ala Asn Leu
          260             265                 270

Asn Asn Gly Gln Gln Arg Leu Ala Leu Arg Gly Phe Thr Ile Phe Pro
          275             280                 285

Val Lys Ser Ile Ile Glu Val Leu Asp Asn Ala Asp Lys Tyr Asp Tyr
    290             295             300

Ile Val Val Asp Glu Ala Gln Arg Leu Arg Gln Asp Leu Gly Glu Gln
305             310             315                     320

Tyr Thr Lys Leu Val Asp Thr Ile Glu Asn Ser Gln Thr Lys Phe Ile
              325                 330             335

Ile Ser Leu Asp Gly Arg Gln Thr Leu Asn Lys Tyr Glu Ile Glu Glu
          340                 345             350

Asn Ser Ile Lys Leu Phe Lys Tyr Ile Lys Asn Lys Gly Val Thr Phe
          355             360             365

Ser Leu Lys Asp Lys Phe Arg Thr Asn Pro Glu Met Ser Lys Phe Ile
    370             375             380

Gln Leu Leu Phe Lys Ile Pro Met Tyr Lys Lys Ile Asp Leu Ile Ser
385             390             395                     400

Asn Ile Asp His Asn Ile Ile Ile Lys Tyr Phe Asp Asn Arg Glu Ser
              405             410             415

Gly Asn Glu Tyr Ile Ser Asp Met Asp Ser Asn Ser Asp Trp Glu Val
              420             425             430

Leu Asn Tyr Thr Lys Asp Arg Phe Arg Lys Thr Gly Ile Gly Lys Met
          435             440             445

Cys Gly Asn Gly Leu Thr Ser His Ser Ile Ile Gly Gln Glu Phe Asp
450                 455             460

Lys Val Ile Ile Pro Leu Asp Ser Asn Phe Phe Tyr Lys Glu Gln Lys
465             470             475                     480

Ile Ile Asp Ser Lys Thr Gly Glu Ser Lys Val Phe Lys Leu Leu Glu
              485             490             495

Thr Thr Asp Asn Phe Tyr Pro Leu Glu Lys Met Leu Tyr Gln Asn Leu
          500             505             510

Thr Arg Thr Arg Gly Lys Ile Glu Phe Val Ile Ile Gly Asn Arg Ser
      515             520             525

Ile Phe Asn Glu Ile Cys Gly Leu Leu Asp Ser Leu
    530             535             540

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear ( i i ) MOLECULE TYPE: DNA (genomic)

( i i i ) HYPOTHETICAL: NO ( i i i ) ANTI-SENSE: NO ( i x ) FEATURE:
            ( A ) NAME/KEY: misc_signal
            ( B ) LOCATION: 3..8
            ( D ) OTHER INFORMATION: /function="EcoRI restriction site"

( i x ) FEATURE:
            ( A ) NAME/KEY: misc_structure
            ( B ) LOCATION: 9..28
            ( D ) OTHER INFORMATION: /function="seq. homologous to
                    nucleotides 1-20 of SEQ ID NO:1"

( x i ) SEQUENCE DESCRIPTION: SEQ ID NO: 3:

GGGAATTCGA ACATAGAATA GATTACGG            28

( 2 ) INFORMATION FOR SEQ ID NO: 4:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
            ( A ) NAME/KEY: misc_signal
            ( B ) LOCATION: 3..8
            ( D ) OTHER INFORMATION: /function="BamHI restriction site"

( i x ) FEATURE:
            ( A ) NAME/KEY: misc_structure
            ( B ) LOCATION: 9..28
            ( D ) OTHER INFORMATION: /function="seq. homolog. to cDNA
                    corresp. to nucleot. 1856-1875 of seq ID No.1"

( x i ) SEQUENCE DESCRIPTION: SEQ ID NO: 4:

GGGGATCCAA ACTGTTCTGT TGCGAGTG            28

( 2 ) INFORMATION FOR SEQ ID NO: 5:

( i ) SEQUENCE CHARACTERISTICS:
            ( A ) LENGTH: 28 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
            ( A ) NAME/KEY: misc_signal
            ( B ) LOCATION: 3..8
            ( D ) OTHER INFORMATION: /function="EcoRI restriction site"

( i x ) FEATURE:
            ( A ) NAME/KEY: misc_structure
            ( B ) LOCATION: 9..28
            ( D ) OTHER INFORMATION: /function="seq. homologous to
                    nucleotides 1292-1311 of SEQ ID NO:1"

( x i ) SEQUENCE DESCRIPTION: SEQ ID NO: 5:

GGGAATTCAA GGAGTAACTT TTAGTCTT            28

( 2 ) INFORMATION FOR SEQ ID NO: 6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: misc_signal
        ( B ) LOCATION: 3..8
        ( D ) OTHER INFORMATION: /function="EcoRI restriction site"

( i x ) FEATURE:
        ( A ) NAME/KEY: misc_structure
        ( B ) LOCATION: 9..28
        ( D ) OTHER INFORMATION: /function="seq. homol. to cDNA
            corresp. to nucleot. 1773-1792 of seq. ID No.1"

( x i ) SEQUENCE DESCRIPTION: SEQ ID NO: 6:

```
GGGAATTCTA AAAATTGAAC GATTTCCA                                              28
```

( 2 ) INFORMATION FOR SEQ ID NO: 7:

( i ) SEQUENCE CHARACTERISTICS:
        ( A ) LENGTH: 3234 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Lactococcus lactis ( x i ) SEQUENCE DESCRIPTION: SEQ ID NO: 7:

```
AAGCTTTACG TCTTGCTTTG AAAATTTCTC AGGTCTTCCT CCAAGTCGTC CTCTTGCACG   60
TGCAGCTTCT CTACCAGCGG CAGAACGCTC CAAAATAAGA TTTCGCTCAA ATTCCGCAAA  120
AGCCGCAAAC AAATGAAACA TCAATTGTCC AGTCGAACTT GATTTATCCA TTGTAATATT  180
TTCTTGCAAG CTATGGAAAC TTACTCCTTT ATCATTAAGT GAATTAACTA TGCTAATTAA  240
GTCCTCCATA TTTCTTCCTA ATCTATCTAA CCGCCAAACA ACAATTGTAT CTCCAGAACG  300
AGAAAATTCG ATGGCGGATT TAAACCAGG  TCTTTCTTTT TTACTTCCTG ACATATGGTC  360
AGTAAATATT TTTTCACAGT TATATTTTTT GAGACTATCT TTTTGTAAAT CCAAATTTTG  420
AAGTCCAGTT GAAACTCGTG CGTATCCTAT ATTCATTTTT TTCTCCTTCA TTTTAATTTA  480
TTGTATCATA ACTTAAAAAT ATATGTATAA ATGAACATAG AATAGATTAC GGGTTAATGG  540
ACAATAAATG CAAACGATTT TGAGAAATTT AATAAGAAAA GAAGAGTGTC CAGAAAATGA  600
CCATTTTCTG AACGCCATAT TAAAATTTT  TTGATAATTC CCAATATATT ATAATATAGC  660
TTCAATGTTA AAATTTATAT GATATAATAT AAGAAAATTT TTAAAAAAAT AGAATGGATA  720
TAATAATGGA CTTTAAAACT ATGTTAAGCT ATCTTGTAAG TCAAGATGAT GAAATTTCTT  780
TAAGAAATGA TATTAAACAT GAAGAAGTAT ATAAAATTTT AGAGAATAAG TTTGCTTCTA  840
TAATGCCGAA GTTTAAAACA AAAGGTTATA AGTTAAAGA  TACTACTGAA GTTTTGACAT  900
```

```
TCGCTAAATT TGTATTTTTG CTACAAGAGT GGGGGTTGAA GGATATACAG TTTTATAAGA   960
ACACTAATAG TTTCTTATTT GGATATATTA TACCGCAAAT TAATAAAGAA TTTGATTTAT  1020
TGAGATTTGG GGAAAATTAC AATATTAGTA TAGAACTCAA AAGTAAAACA ACAGTAGAAG  1080
CACAAAAGCA ACAACTTTGT AAGAACTATT TTTACCTAAA TTTTTATCA  ACTAAAACTA  1140
GGTATATTAG TATATCCCCA GATATATCTA GTTACATAGA ATATATTCCA AGTGAAAATA  1200
AGTATATCAA TTTAAGTGGA ACTGAAATTT GTGATATTAT TATTAAACAA GAGTTTTTAG  1260
AGTATAATAC AAAAGAGGTT GATAGTTTTT TTGATATAAA AAATTATTTA GTTCTCCTT   1320
TCAATGATGT TGAAAAATTT CTGATGATA  AATATTTTTT AACACCTCAC CAAGACCAGA  1380
TTGTTAAAGA AATTACTGAA CCAAGTGACA AAAAAACTTT TGGTATAAAA GGAAATCCAG  1440
GAACAGGAAA ATCTTTGCTA GTTTACCATA TATGTAAAAA ATTAATGGAG AAAAATAAAA  1500
GAGTTGCTAT AGTTCATGGA GCAAATCTAA ATAATGGTCA ACAAGATTA  GCTCTGCGTG  1560
GTTCACAAT  TTTTCCTGTT AAATCGATCA TAGAGGTATT AGATAATGCA GACAAATACG  1620
ATTACATTGT TGTTGACGAA GCTCAACGTC TAAGACAAGA CTTAGGAGAA CAATATACTA  1680
AATTGGTTGA TACTATTGAA AATTCTCAAA CAAAATTTAT TATCTCACTA GATGGAAGAC  1740
AAACTTTGAA TAAATATGAA ATAGAAGAAA ATTCCATAAA ATTATTTAAA TATATAAAAA  1800
ATAAAGGAGT AACTTTTAGT CTTAAAGATA AGTTTAGAAC TAACCCAGAA ATGAGCAAAT  1860
TTATCCAACT TCTATTCAAA ATACCCATGT ATAAAAAAT  AGATTTAATT TCAAACATAG  1920
ATCATAATAT TATAATTAAA TATTTTGATA ACAGAGAATC GGGAAATGAA TATATTTCCG  1980
ATATGGATTC AAACTCAGAT TGGGAAGTAC TTAATTACAC GAAGGATAGA TTTAGGAAAA  2040
CAGGAATTGG TAAAATGTGT GGTAATGGTT TAACATCACA TAGTATTATC GGTCAAGAAT  2100
TTGATAAAGT TATTATACCT TTGGATTCGA ATTTTTTTA  TAAAGAACAA AAAATAATTG  2160
ATAGTAAAAC GGGTGAAAGT AAAGTTTTTA AATTATTGGA AACGACTGAT AATTTTTACC  2220
CACTTGAAAA AATGTTATAT CAAAATCTTA CTCGCACAAG GGGAAAATA  GAATTTGTAA  2280
TTATTGGAAA TCGTTCAATT TTTAATGAAA TATGTGGATT GCTAGATAGT TTATAAAGTT  2340
CTGTCTCAAA GTTAAAAAAA GTGAAATCAC TCGCAACAGA ACAGTTTGAC ATTAAGTCCA  2400
TTTCTTATAC CCAAAAATGT ATAATTCTAA TCTATTTATT TTAGGAAATT ATTTTTTCAA  2460
AATGATTTGG AGTGAGATAC CCCAAACTTT GATGGATTCT TTTAAATAAA ATTTCAAAGC  2520
GCTCACTCCA GAAATGCTAA GTTTCGGAAA AAATTTGAAT TTTTCGTAAA GATATTATTT  2580
TTGGAGTGAA AATCATAAAA TTCTTCTTTT AAAAACTTCC GCAAGTTTTT TAAGGAAAAT  2640
AGTTACTTAC GTCCAAACTC AAAAAATTTT TATAAAATTG TAGTTCATTT GACGGTAAGT  2700
CTTATTATTT AATGATACCT AGTAGTTAAT AATTTGATTA TATTTGTAAT TACAGATATA  2760
ATCAAATTAT TTGGAGGTAT TAATAGTATG GAAAGTAAGT TTAACGGAGA TGAGTCTGGA  2820
TATTATGATA ATAAAGATAA TTTTTATATT AATGGCTCTT TAAAATATAA AGACGATATG  2880
GAAGTTGGTC CAATTTTACA GCATGAGCAT GGACATTGGT TTATTTTTAT GACATCTTCA  2940
CTAGGGCTCT TAATTCGTAT GTGTTCAAAA ATATCAATAA CAGACAATAG TAAAGATTTA  3000
ATTTTGGAGG GATTAAGTAA GTATTATAGA AGAATGAATG AGGAAGTTGC TACATATACT  3060
GAGATGATAA CATATCTTAT GATGAATGGT AGAGAACAAT TCTTCGCAA  AGTTGATTAT  3120
CTAAAATATA ATAATAAGTC ATACTATAAA TACTATAAAA AATTATCTTG TAGAAATATT  3180
TTATTGAGTC AGTCAATGAT TTTAACTTAT GATAAAGAAA AACTTAAAAA GCTT        3234
```

NUCLEIC ACID SEQUENCE AND PLASMIDS COMPRISING AT LEAST ONE PHAGE RESISTANCE MECHANISM, BACTERIA IN WHICH THEY ARE PRESENT, AND THEIR USE

The present invention relates to a novel nucleic acid sequence and plasmids capable of hybridizing therewith which carry at least one phage resistance mechanism, to the lactic acid bacteria in which this sequence or these plasmids are present, in particular the lactococci belonging to the species *Lactococcus lactis*, to the use of certain strains of these lactococci for the transfer, especially by conjugation, of a phage resistance mechanism to strains of industrial interest, in particular in the dairy industry, and to the use of certain strains of *Lactococcus lactis* for the preparation of these plasmids.

Lactic acid bacteria are involved in the production and storage of a large number of food products such as cheese, butter, yogurt, sausage or pickled cabbage. Dairy products are of particular importance among these foods. The industrial processing of milk is carried out in ever larger fermentation vats, in which the appearance of phages of lactic acid bacteria can have serious or even catastrophic consequences, namely a variation in the characteristics, especially organoleptic characteristics, of the final product, the loss of the product present in the vat, and the need to decontaminate the latter as well as the surrounding installations. The dairy industry therefore has a pressing need for new means and new methods by which lactic acid bacteria can be rendered more resistant to phages.

The phages of lactic acid bacteria belong to three major homology groups, (I), (II) and (III), defined by DNA/DNA hybridization studies according to RELANO P. et al., (1987), J. Gen. Microbiol. 133, 3053–3063. Groups (I) and (III) comprise only virulent phages. Group (II) comprises virulent phages and temperate phages. The homologies are strong within one and the same group and very weak between groups. Group (I) phages have an oblong nucleocapsid, whereas group (I) and (III) phages have an isometric nucleocapsid.

Several phage resistance mechanisms are known to exist, the three main ones being:

the inhibition of phage adsorption; in this mechanism, the adsorption of the phage by the bacterium is inhibited or delayed.

the restriction/modification system; this system involves a restriction enzyme which degrades the phage DNA as soon as it enters the bacterium.

abortive infection; according to this third mechanism, the phages are adsorbed normally but do not multiply.

These mechanisms are described in detail by SANDERS M. in Biochimie 70, (1988), 411–421.

Numerous studies have already been carried out with the aim of developing phage-resistant lactic acid bacteria.

In this connection, reference may be made in particular to the following articles:

VLEGELS et al., Neth. Milk and Dairy J. 43, (1989), 245–259;

SANDERS and KLAENHAMMER, Applied and Environ. Microbiol. (1983), vol. 46, 1125–1133, relating to plasmids which inhibit phage adsorption;

Audrey W. JARVIS, Applied and Environ. Microbiol. March 1988, p.777–783;

EP-A3-0 208 468;

COFFEY et al., Neth. Milk and Dairy J. 43, (1989), 229–244;

KLAENHAMMER and SANOZKY, Journal of General Microbiology (1985), 131, 1531–1541, describing plasmids which confer phage resistance by the abortive infection mechanism;

JOSEPHSEN and KLAENHAMMER, Plasmid 23, 71–75, (1990);

U.S. Pat. No. 4,883,756;

GAUTIER and CHOPIN, Applied and Environ. Microbiology (1987), 53, p. 923–927, the two latter articles especially describing plasmids which confer phage resistance by the restriction/modification mechanism.

The Applicants have also worked in this field and described in EP-A1-452 224 as well as in U.S. patent application Ser. No.08/144,611 filed on Nov. 1st, 1993 as a continuation of U.S. Pat. No. 07/778,097 of Dec. 13, 1991, both incorporated herein by way of reference, a DNA molecule comprising at least one phage resistance mechanism, said molecule containing a functional part of the HindIII—HindIII fragment of about 3.3 kb of plasmid pPF144-1 present in the strain of *Escherichia coli* deposited in the National Collection of Cultures of Microorganisms (CNCM) of the Pasteur Institute, Paris under no. I-1070 on 9th Apr. 1991.

This HindIII—HindIII fragment of about 3.3 kb was isolated from plasmid pPF144 contained in the strain *Lactococcus lactis* ssp *lactis*, deposited in the CNCM under no. I-945, which is a transconjugant derived from the crossing of the donor strain *Lactococcus lactis* ssp *lactis* S91, deposited in the CNCM under no. I-940 on 12th Apr. 1990, with the recipient strain *Lactococcus lactis* ssp *lactis* S45, derived from the strain *Lactococcus lactis* ssp *lactis* C2-L. L. McKay et al., 1977, J. Bacteriol. 257–265. This fragment carries one or more phage resistance mechanisms.

Continuing their work, the Applicants isolated, from this HindIII—HindIII DNA sequence of 3.3 kb, a DNA sequence of 1.9 kb which on its own confers phage resistance.

The present invention therefore relates to a novel nucleic acid sequence comprising at least one phage resistance mechanism, said sequence having about 1.9 kb and consisting of:

a) the DNA sequence having the nucleic acid series of SEQ ID no. 1;

b) the DNA sequences hybridizing with the above sequence or a fragment thereof; and c) the corresponding mRNA and cDNA sequences.

The sequence [SEQ ID no. 2] is the amino acid sequence deduced from sequence SEQ ID no. 1.

The DNA sequence [SEQ ID no. 1] can be obtained from the HindIII—HindIII DNA sequence of 3.3 kb contained in the strain *Lactococcus lactis* ssp *lactis*, deposited in the CNCM under no. I-945, by the PCR method using the following two oligonucleotides:

Oligonucleotide no. 1 [SEQ ID no. 3]:
5'     GGGAATTCGAACATAGAATAGATTACGG     3'
       EcoRI
Oligonucleotide no. 2 [SEQ ID no. 4]:
5'     GGGGATCCAAACTGTTCTGTTGCGAGTG     3'
       BamHI The invention further relates to the DNA sequences which have a high degree of homology with the above DNA sequence [SEQ ID no. 1]. Here a high degree of homology means a homology (ratio of the identical nucleotides to the total number of nucleotides) of at least 70%, preferably at least 80%, of the nucleotide sequences when they are aligned according to maximum homology, using the optimal sequence alignment method of Needleman and Wunsch, 1970, J. Mol. Biol. 48, 443–453. This method is used especially in the UWGCG software of the University of Wisconsin: Devereux et al., 1984, Nucl. Ac. Res. 12, 8711–8721-option GAP.

The present invention particularly relates to the DNA sequences which hybridize with the DNA sequence [SEQ ID no. 1] or a fragment thereof. In the present specification the term "hybridization" designated the conventional hybridization conditions and more particularly the stringent hybridization conditions.

The invention further relates to the plasmids transformed with one of the nucleic acid sequences according to the invention. These plasmids can be for example plasmid pPF144-12 into which the DNA sequence according to the invention has been cloned by the usual techniques well known to those skilled in the art.

The invention further relates to the phage-resistant lactic acid bacteria, preferably belonging to the species *Lactococcus lactis*, which contain at least one nucleic acid sequence or one plasmid as defined above.

This nucleic acid sequence or this plasmid may have been introduced into the lactic acid bacteria by conjugation, transformation, protoplast fusion or another gene transfer method.

Examples of the lactic acid bacteria which can advantageously be transformed with the nucleic acid sequence according to the invention or a plasmid containing said sequence are the strains *Lactococcus lactis* ssp *cremoris*, *Lactococcus lactis* ssp *lactis* and *Lactococcus lactis* ssp *lactis var. diacetylous*.

These strains, transformed in this way, can be used for the transfer, by conjugation, transformation, transduction, protoplast fusion or another gene transfer method, of a phage resistance mechanism to a strain of industrial interest. This mechanism can be carried by a plasmid or by another part of the genome of the bacterium. If said mechanism is carried by a plasmid, it is advantageously transferred by conjugation.

The invention further relates to the resulting phage-resistant strains of industrial interest.

The invention will be understood more clearly with the aid of the following Examples, which include experimental results and a discussion thereof. Some of these Examples relate to experiments performed in order to carry out the invention; other Examples of how to carry out the invention are of course given purely by way of illustration.

A large part of all the techniques described in these Examples, which are well known to those skilled in the art, is described in detail in the work by Sambrook, Fritsch and Maniatis: "Molecular cloning; a Laboratory Manual" published in 1989 by Cold Spring Harbor Press in New York (2nd edition).

The following description will be understood more clearly with the aid of FIGS. 1 and 2 below, in which:

FIG. 1 shows the restriction map of the 3.3 kb fragment of pPF144-1. Tn552 is a region having a high degree of Homology with part of transposon Tn552. The term "ORF" signifies an open reading frame of 1620 bp. IS981 is a region having a high degree of homology with part of insertion sequence IS981. The term "orf" signifies the beginning of an open reading frame.

Figure 2:
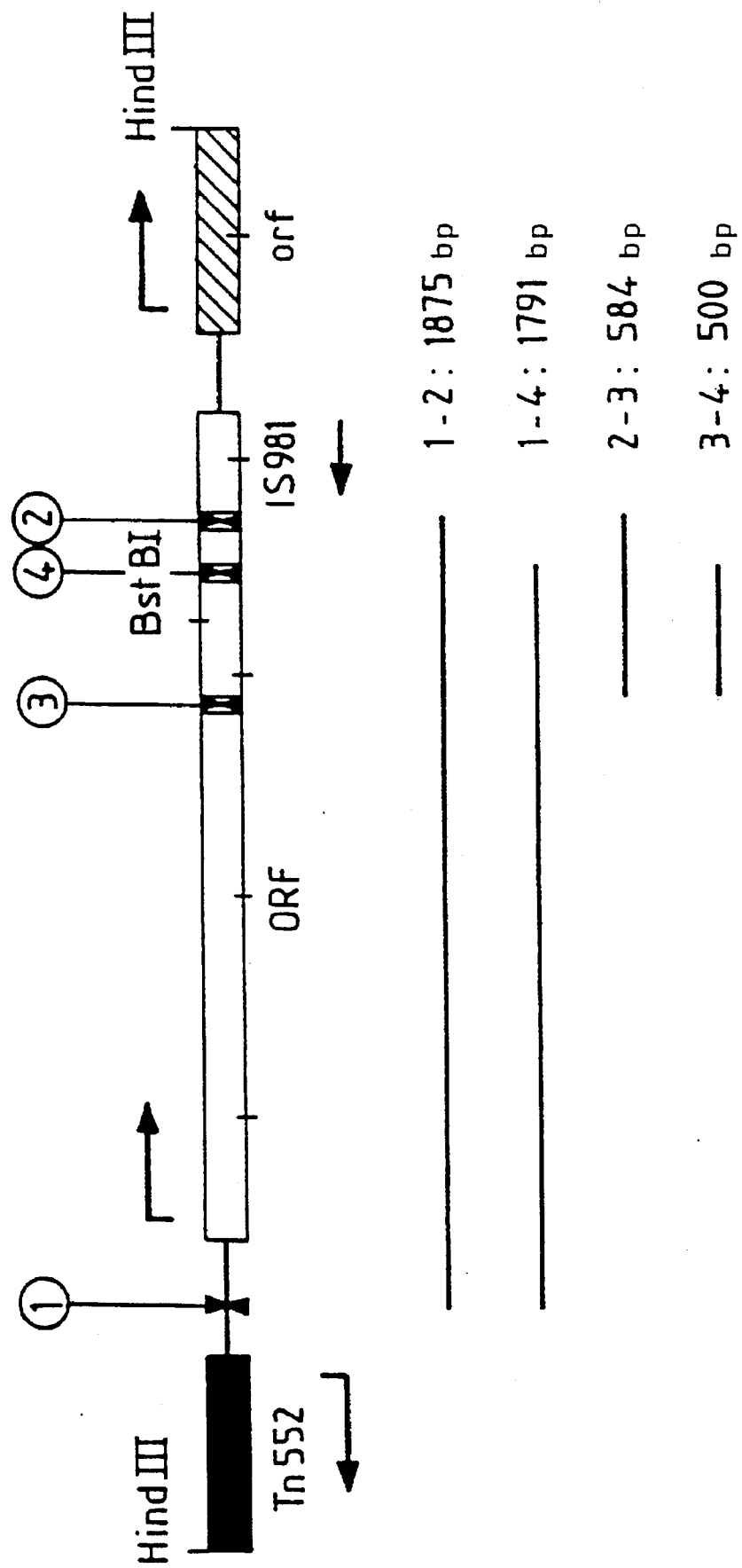

FIG. 2 shows the amplification by the PCR method of internal fragments of the 3.3 kb fragment of pPF144-1.

Fragment 1-2 confers phage resistance.

Fragments 1-4, 2-3 and 3-4 do not confer phage resistance.

EXAMPLE 1

Sequence of the HindIII—HindIII fragment of 3.3 kb

The strain *Lactococcus lactis* S45-91-1, deposited in the CNCM under no. I-945 on 12th Apr. 1990, contains a plasmid with a size of 144 kb, called pPF144, which confers phage resistance. This strain is totally resistant to phage Ø59 (group III). On the other hand, it has a partial resistance to phage Ø53 of group I, which develops but forms abnormally small lysis plates of the size of a pinhead. The HindIII—HindIII restriction fragment of 3.3 kb, conferring phage resistance, was cloned from plasmid pPF144 in vector pVA838 disclosed by MACRINA F. L. et al (1982), Gène, 19, 345–353, according to the procedure disclosed in Example 7 of EP-A1-452 224 and of U.S. Ser. No.08/144,611, incorporated herein by way of reference. This recombinant plasmid, pPF144-2, confers on the strain *Lactococcus lactis* ssp *lactis* S56 the same level of phage resistance as plasmid pPF144 in its entirety.

The nucleic acid sequence of this 3.3 kb fragment, determined by the method of Sanger et al. (PNAS-USA, 14, 5463, 1977), is the sequence [SEQ ID no. 7] below.

Enzymic restriction analyses of this 3.3 kb fragment showed the presence in this fragment of a single site for recognition of the enzyme BstBI. Subcloning of the two HindIII-BstBI restriction fragments and their introduction into the strain *L. lactis* S56 made it possible to show that neither of them confers phage resistance. From this it was deduced that the BstBI site is within the assumed resistance gene. This hypothesis was strengthened by determination of the nucleotide sequence of the two fragments, showing that the BstBI site is within an open reading frame (ORF) of 1.62 kb, which would correspond to the resistance gene. FIG. 1 shows the restriction map of the HindIII—HindIII fragment of 3.3 kb.

Other analyses also showed that the HindIII—HindIII fragment of 3.3 kb possesses:

a region Tn552 having a high degree of homology with part of transposon Tn552 (ref.: Tn552, a novel transposable element from *Staphylococcus aureus* (1990), S. J. ROWLAND, K. G. H. DYKE, Molecular Microbiology 4, 961–975);

an ORF of 1620 bp which would correspond to the resistant gene;

a region IS981 having a high degree of homology with part of insertion sequence IS981. (ref.: Identification, DNA sequence and distribution of IS98, a new high-copy-number insertion sequence in Lactococci (1991), K. M. POLZIN, L. L. McKAY, Applied and Environ. Microbiol. 57, 734–743;

the beginning of an open reading frame (orf).

EXAMPLE 2

Amplification by the PCR method of internal fragments of the HindIII—HindIII fragment of 3.3 kb The "PCR" (Polymerase Chain Reaction) technique, described for example in the work by Maniatis cited above, makes it possible to amplify a DNA fragment located between two oligonucleotides. This amplified DNA can easily be cloned if restriction sites are provided by the oligonucleotides. In fact, the sequences of these oligonucleotides can contain, at their 5' end, a heterologous part of the DNA to be amplified, consisting for example of 8 base pairs, 6 of which constitute a restriction site.

This technique was applied in order to determine whether the ORF revealed in the nucleotide sequence of the 3.3 kb fragment did indeed correspond to the phage resistance gene, but also in order to form a specific probe for this ORF.

4 oligonucleotides of 28 bases (6 of which constitute a restriction site) were synthesized.

These 4 oligonucleotides have the following sequences:

Oligonucleotide no. 1 [SEQ no. 3]:
5'      GGG<u>AATTC</u>GAACATAGAATAGATTACGG      3'
        EcoRI
Oligonucleotide no. 2 [SEQ no. 4]:
5'      GGG<u>GATCC</u>AAACTGTTCTGTTGCGAGTG      3'
        BamHi
Oligonucleotide no. 3 [SEQ no. 5]:
5'      GGG<u>AATTC</u>AAGGAGTAACTTTTAGTCTT      3'
        EcoRI
Oligonucleotide no. 4 [SEQ no. 6]:
5'      GGG<u>AATTC</u>TAAAAATTGAACGATTTCCA      3'
        EcoRI Their locations on the 3.3 kb fragment are indicated in FIG. 2.

Oligonucleotides no. 1 and 2 made it possible to amplify a DNA fragment of 1875 bp containing the entire ORF plus 201 bp directly upstream of the latter, a region capable of containing gene expression signals. This DNA was amplified in the form of an EcoRI-BamHI fragment by virtue of the restriction sites provided by the oligonucleotides, allowing a directional cloning in shuttle vector pVA838.

In the same way, oligonucleotides no. 3 and 4 made it possible to amplify a region of 500 bp, overlapping the BstBI site, in the form of an EcoRi-EcoRi fragment. This region was chosen for forming a specific probe since it was shown that the two HindIII-BstBI subfragments of the 3.3 kb fragment did not on their own confer phage resistance, and hence that the region of the BstBI site was essential for the activity of the gene.

Two other fragments within the ORF could be amplified by the "PCR" method by virtue of the oligonucleotide pairs no. 1 and 4 and no. 2 and 3.

Starting from plasmid pPF144-2 purified on CsCl, the 4 DNA fragments were amplified by the "PCR" method with Vent polymerase (Biolabs), which possesses an exonuclease activity increasing its fidelity by a factor of 15 compared with the conventional Taq polymerase. The PCR products were purified by extraction with phenol/chloroform, precipitated with ethanol, digested with EcoRI or BamHI and EcoRI, depending on the fragment, and cloned in vector pVA838.

Cloning of the fragments in vector pVA838 made it possible to introduce them into a strain of L. lactis, after amplification of the recombinant plasmids in the strain E. coli TG1, and to determine whether they confer phage resistance.

A synopsis of the results relating to the cloning of the different amplified DNA fragments is presented in Table I below:

TABLE I

| Oligonucléotide pair | Fragment size | Added sites | Cloned in pVA838 |
|---|---|---|---|
| 1-2 | 1875 pb | EcoRI-BamHI | pPF144-12 |
| 1-4 | 1791 pb | EcoRI-EcoRI | pPF144-14 |
| 2-3 | 584 pb | BamHI-EcoRI | pPF144-23 |
| 4-3 | 500 pb | EcoRI-EcoRI | pPF144-43 |

EXAMPLE 3

Phage resistance conferred by plasmid pPF144-12

Plasmids pPF144-12, pPF144-14, pPF144-23 and pPF144-43 were introduced into the strain L. lactis S56. The phage resistance of the clones obtained was tested by performing a titration (PFU/ml) with phages Ø53 and Ø59.

The results are given below:

| Strain | phage Ø53 (I) | | phage Ø59 (III) | |
|---|---|---|---|---|
| | Titer (PFU/ml) | Plate size (mm) | Titer (PFU/ml) | Plate size (mm) |
| S56 | $10^{10}$ | 3 | $3.10^9$ | 2 |
| S56(pPF144-1) | $2.10^7$ | <0,25 | 0 | 0 |
| S56(pPF144-12) | $4.10^7$ | <0,25 | 0 | 0 |
| S56(pPF144-14) | $8.10^9$ | 3 | $6.10^9$ | 2 |
| S56(pPF144-23) | $6.10^9$ | 3 | $6.10^9$ | 2 |
| S56(pPF144-43) | $10^{10}$ | 3 | $2.10^9$ | 2 |

PFU/ml = plate forming units per ml

Plasmid pPF144-12, containing the 1875 bp fragment amplified by the PCR method, confers the same phage resistance as plasmid pPF144-1. The other plasmids, namely pPF144-14, pPF144-23 and pPF144-43, comprising only part of the ORF of 1.62 kb, do not confer phage resistance.

EXAMPLE 4

Test on the replication of phage DNA in the presence of plasmid pPF144-12

Phages Ø53 and Ø59 belong to genetic groups I and III respectively. A genetic map of these phages was constructed and it was demonstrated in particular that the genome of these phages, consisting of double-stranded DNA, possesses sticky ends. This result implies that the replication of the DNA of these phages takes place according to a model identical to that of E. coli phage lambda: formation of concatemers during the lytic cycle and cleavage of these concatemers with a specific enzyme at the moment of encapsidation in the nucleocapsid of the phage.

The method of Hill et al. (Hill, C., Massey, I. J., Klaenhammer, T. R. (1991), Rapid method to characterize lactococcal bacteriophage genomes, Appl. Environ. Microbiol. 57, 283-288) was used to follow the fate of the phage DNA after injection into the bacterium. The strain L. lactis S56, containing the vector pVA838 or the plasmid pPF144-12, was infected with Ø53 and Ø59 with a multiplicity of infection of 2. Aliquots of the infected cultures are taken at regular intervals of time. The total DNA, i.e. cell and phage DNA, of each aliquot is extracted and digested with a restriction enzyme and the fragments obtained are separated electrophoretically by migration on agarose gel. The DNA is then transferred to a nylon membrane and hybridized with the DNA of the phage used as the probe (ECL kit, Amersham).

This method makes it possible to follow the appearance of, and change in, the phage DNA within the infected cell as a function of time.

The results obtained with the enzymes EcoRI, HindIII and EcoRV showed that the phage DNA replicates in the S56 strains with the vector pVA838 or the plasmid pPF144-12. An accumulation of the phage DNA in the form of concatemers is observed with the plasmid pPF144-12, whereas in the strain containing the vector pVA838, these concatemers start to disappear twenty minutes after infection.

EXAMPLE 5

Test on the production of phage proteins in the presence of plasmid pPF144-12

Phage Ø53 and Ø59 preparations purified on cesium chloride were used to prepare polyclonal antibodies in rabbits. The 56 strain, containing the vector pVA838 (control) or the plasmid pPF144-12, was infected with one of these phages with a multiplicity of 1. Every five minutes after infection, a fraction of the cells is taken and heated for three minutes at 100° C. in the presence of 2.3% of SDS and 5% of β-mercaptoethanol and the proteins are fractionated on a 12.5% SDS-polyacrylamide gel [Laemmli, U. K. 1970, Cleavage of structural proteins during the assembly of the head of bacteriophage T4, NATURE (London) 227, 680–685] and then transferred to nitrocellulose filters.

Immunological detection of the phage proteins on the nitrocellulose was effected with anti-Ø53 or anti-Ø59 rabbit antibodies and the immune complex was then localized with anti-rabbit mouse antibodies (ECL kit, Amersham) using streptavidin/alkaline phosphatase.

These results show that the proteins of phage Ø53 or Ø59 are found with and without the plasmid pPF144-12, but that, in the presence of this plasmid, the amount of proteins produced is small and the rate of appearance of these proteins is slowed down compared with a strain containing the vector pVA838. This phenomenon is more pronounced for Ø59 than for Ø53.

What is claimed is:

1. A polynucleotide conferring at least one phage resistance mechanism, wherein said polynucleotide encodes a polypeptide according to SEQ ID NO:2.

2. A plasmid encoding at least one phage resistance mechanism, said plasmid containing a polynucleotide encoding a polypeptide according to SEQ ID NO:2.

3. A method of conferring phage resistance to a bacterium, comprising the step of contacting said bacterium with a polynucleotide encoding a polypeptide according to SEQ ID NO:2.

4. A method according to claim 3, wherein said contacting occurs through conjugation or fusion.

5. A method according to claim 3, wherein said contacting occurs through transformation.

* * * * *

UNITED STATES PATENT AND TRADEMARK OFFICE
CERTIFICATE OF CORRECTION

PATENT NO. : 5,658,770
DATED : August 19, 1997
INVENTOR(S) : PREVOTS et al.

It is certified that error appears in the above-identified patent and that said Letters Patent is hereby corrected as shown below:

Title page, item [73] Assignees: Please delete "SANOFI, Paris, France", and insert --SYSTEMS BIO-INDUSTRIES, Boulogne- Billancourt Cedex, France--.

Signed and Sealed this

Sixteenth Day of December, 1997

Attest:

BRUCE LEHMAN

*Attesting Officer*   *Commissioner of Patents and Trademarks*